United States Patent
Yanagawa et al.

(10) Patent No.: US 9,255,042 B2
(45) Date of Patent: Feb. 9, 2016

(54) PRODUCING METHOD OF MONOCYCLIC AROMATIC HYDROCARBONS AND MONOCYCLIC AROMATIC HYDROCARBON PRODUCTION PLANT

(75) Inventors: Shinichiro Yanagawa, Tokyo (JP); Yasuyuki Iwasa, Tokyo (JP); Susumu Yasui, Yokohama (JP); Yoshishige Sugi, Yokohama (JP); Atsushi Fukui, Kawasaki (JP); Atsuro Nagumo, Kawasaki (JP)

(73) Assignees: JX Nippon Oil & Energy Corporation, Tokyo (JP); CHIYODA CORPORATION, Yokohama-shi, Kanagawa (JP)

( * ) Notice: Subject to any disclaimer, the term of this patent is extended or adjusted under 35 U.S.C. 154(b) by 256 days.

(21) Appl. No.: 14/119,571
(22) PCT Filed: May 24, 2012
(86) PCT No.: PCT/JP2012/063345
§ 371 (c)(1),
(2), (4) Date: Feb. 20, 2014
(87) PCT Pub. No.: WO2012/161261
PCT Pub. Date: Nov. 29, 2012

(65) Prior Publication Data
US 2014/0163275 A1 Jun. 12, 2014

(30) Foreign Application Priority Data
May 24, 2011 (JP) ................................. 2011-115642

(51) Int. Cl.
*C07C 2/42* (2006.01)
*C10G 35/00* (2006.01)
(Continued)

(52) U.S. Cl.
CPC . *C07C 4/06* (2013.01); *B01D 3/009* (2013.01); *B01J 29/047* (2013.01); *B01J 29/048* (2013.01);
(Continued)

(58) Field of Classification Search
CPC ........... C07C 2/42; C10G 35/00; C10G 15/00
USPC ............................ 585/418; 208/133, 134, 106
See application file for complete search history.

(56) References Cited

U.S. PATENT DOCUMENTS

2012/0012504 A1   1/2012 Minami et al.

FOREIGN PATENT DOCUMENTS

| CN | 1246516 A | 3/2000 |
|---|---|---|
| CN | 101362961 A | 2/2009 |

(Continued)

OTHER PUBLICATIONS

Int'l Search Report issued Aug. 28, 2012 in Int'l Application No. PCT/JP2012/063345.

(Continued)

*Primary Examiner* — Thuan D Dang
(74) *Attorney, Agent, or Firm* — Panitch Schwarze Belisario & Nadel LLP

(57) ABSTRACT

A producing method of monocyclic aromatic hydrocarbons from the oil feedstock having a 10 volume % distillation temperature of more than or equal to 140° C. and a 90 volume % distillation temperature of less than or equal to 380° C. by bringing into contact with an aromatic production catalyst includes the steps of: introducing the oil feedstock into a cracking and reforming reaction apparatus housing the aromatic production catalyst; bringing the oil feedstock and the aromatic production catalyst into contact with each other at the inside of the cracking and reforming reaction apparatus; heating the oil feedstock in advance before introducing the oil feedstock into the cracking and reforming reaction apparatus and forming a two-phase gas-liquid stream; separating the two-phase gas-liquid stream into a gas fraction and a liquid fraction; and introducing the gas fraction and the liquid fraction at different positions of the cracking and reforming reaction apparatus.

3 Claims, 1 Drawing Sheet

(51) Int. Cl.
*C10G 15/00* (2006.01)
*C07C 4/06* (2006.01)
*B01J 29/40* (2006.01)
*B01J 29/70* (2006.01)
*B01J 29/87* (2006.01)
*B01D 3/00* (2006.01)
*C10G 35/14* (2006.01)
*C10G 35/24* (2006.01)
*C10G 49/26* (2006.01)
*C10G 11/18* (2006.01)
*B01J 29/04* (2006.01)
*B01J 29/08* (2006.01)
*B01J 29/18* (2006.01)
*B01J 29/82* (2006.01)
*B01J 29/86* (2006.01)

(52) U.S. Cl.
CPC  *B01J 29/08* (2013.01); *B01J 29/18* (2013.01); *B01J 29/185* (2013.01); *B01J 29/40* (2013.01); *B01J 29/70* (2013.01); *B01J 29/7007* (2013.01); *B01J 29/7057* (2013.01); *B01J 29/82* (2013.01); *B01J 29/86* (2013.01); *B01J 29/87* (2013.01); *C10G 11/187* (2013.01); *C10G 35/14* (2013.01); *C10G 35/24* (2013.01); *C10G 49/26* (2013.01); *B01J 2229/186* (2013.01); *C10G 2300/301* (2013.01); *C10G 2400/30* (2013.01)

(56) References Cited

FOREIGN PATENT DOCUMENTS

| | | |
|---|---|---|
| JP | 2010-532752 A | 10/2010 |
| WO | 2009008876 A1 | 1/2009 |
| WO | 2010109899 A1 | 9/2010 |
| WO | 2011118753 A1 | 9/2011 |

OTHER PUBLICATIONS

Office Action issued Aug. 27, 2014 in CN Application No. 201280024818.6.

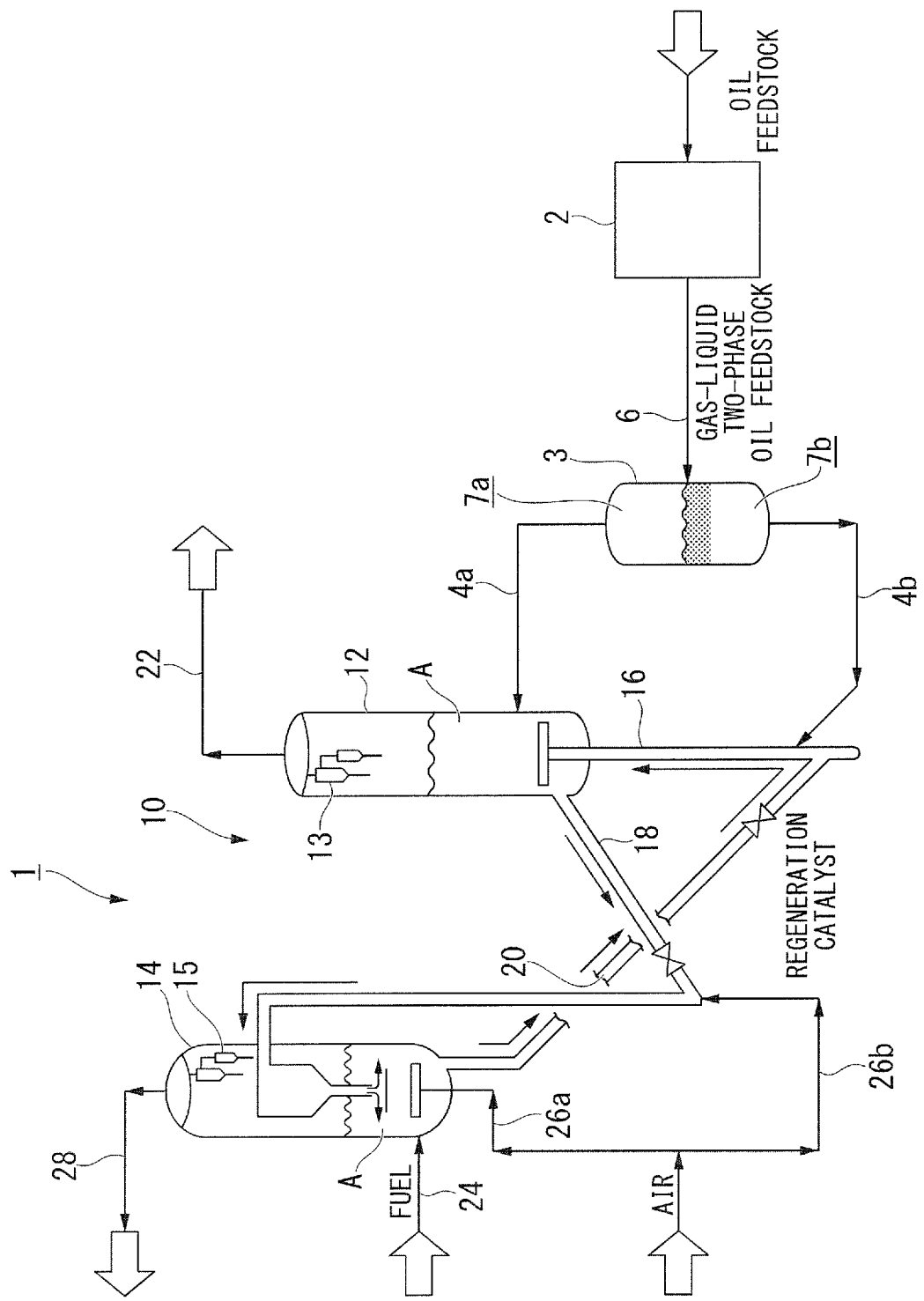

PRODUCING METHOD OF MONOCYCLIC AROMATIC HYDROCARBONS AND MONOCYCLIC AROMATIC HYDROCARBON PRODUCTION PLANT

CROSS-REFERENCE TO RELATED APPLICATION

This application is a Section 371 of International Application No. PCT/JP2012/063345, filed Mar. 24, 2012, which was published in the Japanese language on Nov. 29, 2012, under International Publication No. WO 2012/161261 A1, and the disclosure of which is incorporated herein by reference.

TECHNICAL FIELD

The present invention is related to a producing method of monocyclic aromatic hydrocarbons and a monocyclic aromatic hydrocarbon production plant, and in particular, a producing method of monocyclic aromatic hydrocarbons by a cracking and reforming by using a fluidized-bed (hereafter, represent as "a cracking and reforming reaction").

Priority is claimed on Japanese Patent Application No. 2011-115642, filed May 24, 2011, the contents of which are incorporated herein by reference.

BACKGROUND ART

Methods of producing monocyclic aromatic hydrocarbons such as BTX (benzene, toluene and xylene) from an oil feedstock such as a cracked light oil (hereinafter light cycle oil and also abbreviated as "LCO") containing a large amount of polycyclic aromatics obtained from a fluid catalytic cracking (hereinafter also abbreviated as "FCC") unit, or a light naphtha, heavy naphtha or the like obtained from a crude oil distillation unit, using a catalytic aromatic production reaction that employs an aromatic production catalyst are already well known.

The production systems of aromatic hydrocarbons using aromatic production catalyst generally employ a fixed bed system, a moving bed system or a fluidized-bed system. In Patent Document 1, a producing method of monocyclic aromatic hydrocarbons employing a fluidized-bed system is disclosed. In a cracking and reforming apparatus employing fluidized-bed system, the aromatic production catalyst and the feedstock can maintain in a state of similar to a complete mixing, and the reaction temperature becomes easy to maintain uniformly. In addition, the aromatic production catalyst, which is deteriorated by coke in a case where the feedstock becomes heavier, is withdrawn appropriately from the cracking and reforming reactor, and an adhered coke is burned, and thereby heating the aromatic production catalyst can be performed smoothly.

PRIOR ART DOCUMENTS

Patent Documents

[Patent Document 1] Pamphlet of International publication No. 2010/109899

DISCLOSURE OF THE INVENTION

Problems to be Solved by the Invention

In the above conventional art, heating of the oil feedstock is performed by maintaining a large amount of heat from the cracking and reforming reactor and exchanging heat with produced oil that has been supplied from the distillation tower, when introduced into the reactor. In this case, the property of the oil feedstock of the conventional art is high in distillation point, and thus, the feedstock does not much vaporize by heating, and is introduced in a state of liquid phase, is vaporized in the inside of the riser pipe, and is provided to reaction by contacting with a fluidized-bed catalyst. However, the LCO, which is the oil feedstock used in the present invention, is low in distillation point, and when exchanging heat with the above reaction product, the oil feedstock is good vaporized and becomes in a gas-liquid two-phase state.

If the oil feedstock being in such the gas-liquid two-phase state is introduced into the riser pipe, there is a problem that vibration may be generated when the oil feedstock is introduced thereinto. More specifically, in a two-phase gas-liquid stream, the flow resistance of a gas fraction and a liquid fraction are different from each other due to the difference of their viscosities and the like. Thus, for example, when the oil feedstock is introduced into the riser pipe through the feed pipe, the flow resistance changes repeatedly in the vicinity of the introducing part by the difference of each flow resistance, and as a result, the pipe vibrates.

As the countermeasure of this, reducing the load of exchanging heat with the produced oil and not increasing too much temperature of the oil feedstock can be considered. However, as the result, a recovery of the heat amount included in the products becomes insufficient, and the balance would be lost in terms of the heat balance of the process. In addition, when the oil feedstock is wholly vaporized by pre-heating by using the heating device (a furnace, a heat exchanger and the like), the oil feedstock passes through the dew point in the furnace and slugs are accumulated on the surface of the furnace, or the like, and as the result, it leads to an excessive temperature rise and it causes concomitant problems of coking and corrosion.

The present invention has been made in view of the above problems, the present invention provides a producing method of monocyclic aromatic hydrocarbons and a monocyclic aromatic hydrocarbon production plant in which it can suppress a generation of vibration when the feedstock is introduced and reduce problems in the process.

Means for Solving the Problem

In order to solve the above problems, one aspect of the present invention provides a producing method of monocyclic aromatic hydrocarbons producing reaction products including monocyclic aromatic hydrocarbons by bringing an oil feedstock and an aromatic production catalyst into contact with each other, the oil feedstock having a 10 volume % distillation temperature of more than or equal to 140° C. and a 90 volume % distillation temperature of less than or equal to 380° C., the method including the steps of: introducing the oil feedstock into a cracking and reforming reaction apparatus housing the aromatic production catalyst; bringing the oil feedstock and the aromatic production catalyst into contact with each other in the cracking and reforming reaction apparatus housing the aromatic production catalyst; heating the oil feedstock in advance before introducing the oil feedstock into the cracking and reforming reaction apparatus and forming a two-phase gas-liquid stream; separating the two-phase gas-liquid stream into a gas fraction and a liquid fraction; and introducing the gas fraction and the liquid fraction at different positions of the cracking and reforming reaction apparatus.

In the producing method of the monocyclic aromatic hydrocarbons according to another aspect of the present invention, the cracking and reforming reaction apparatus is provided with a cracking and reforming reactor housing the aromatic production catalyst, a heat tank heating the aromatic production catalyst withdrawn from the inside of the cracking and reforming reactor by a combustion, and a catalyst transfer pipe transferring the aromatic production catalyst heated at the heat tank to the cracking and reforming reactor, and in the step of introducing the gas fraction and the liquid fraction, at least the liquid fraction may be introduced into the catalyst transfer pipe.

In addition, in the producing method of monocyclic aromatic hydrocarbons according to another aspect of the present invention, in the step of introducing the gas fraction and the liquid fraction, at least the gas fraction may be introduced into the cracking and reforming reactor.

In addition, another aspect of the present invention provides a monocyclic aromatic hydrocarbons production plant in which reaction products including monocyclic aromatic hydrocarbons are produced by bringing an oil feedstock and an aromatic production catalyst into contact with each other, the oil feedstock having a 10 volume % distillation temperature of more than or equal to 140° C. and a 90 volume % distillation temperature of less than or equal to 380° C., the production plant including: a cracking and reforming reaction apparatus housing the aromatic production catalyst, a heating device heating the oil feedstock in advance before introducing the oil feedstock into the cracking and reforming reaction apparatus and forming a two-phase gas-liquid stream; a separator separating the two-phase gas-liquid stream into a gas fraction and a liquid fraction; and introducing device introducing the gas fraction and the liquid fraction at different positions of the cracking and reforming reaction apparatus.

In addition, in the monocyclic aromatic hydrocarbon production plant according to another aspect of the present invention, the cracking and reforming reaction apparatus is provided with a cracking and reforming reactor housing the aromatic production catalyst, a heat tank heating the aromatic production catalyst withdrawn from the inside of the cracking and reforming reactor by a combustion, and a catalyst transfer pipe transferring the aromatic production catalyst heated at the heat tank to the cracking and reforming reactor, and the introducing device may introduce at least the liquid fraction into the catalyst transfer pipe.

In addition, in the monocyclic aromatic hydrocarbon production plant according to another aspect of the present invention, the introducing device may introduce at least the gas fraction into the cracking and reforming reactor.

Effects of the Invention

According to the producing method of the monocyclic aromatic hydrocarbons and the monocyclic aromatic hydrocarbon production plant of the present invention, it can suppress the generation of vibration when the feedstock is introduced and reduce problems in the process.

BRIEF DESCRIPTION OF THE DRAWINGS

FIG. 1 is a schematic structural diagram illustrating one example of a monocyclic aromatic hydrocarbon production plant 1 according to the present invention.

EMBODIMENTS OF THE INVENTION

Monocyclic Aromatic Hydrocarbon Production Plant

FIG. 1 is a schematic structural diagram illustrating one example of a monocyclic aromatic hydrocarbon production plant 1 according to the present invention.

The monocyclic aromatic hydrocarbon production plant 1 is provided with a cracking and reforming reaction apparatus 10, a heating device 2, a gas-liquid separator 3, and feed pipes (an introducing device) 4a, 4b. The cracking and reforming reaction apparatus 10 is an apparatus in which an oil feedstock is brought into contact with an aromatic production catalyst A, and thereby obtaining reaction products including monocyclic aromatic hydrocarbons, and the apparatus is provided with a cracking and reforming reactor 12, a heating tank 14, and a catalyst riser 16 (a catalyst transfer pipe). In addition, the cracking and reforming reaction apparatus 10 is provided with a withdrawing pipe 18, a return pipe 20, a reaction product pipe 22, a fuel pipe 24, an air pipe 26a, 26b, and an exhaust pipe 28. One end of the withdrawing pipe 18 is connected to the cracking and reforming reactor 12, and another end of the withdrawing pipe 18 is connected to the heating tank 14. One end of the return pipe 20 is connected to the heating tank 14, and another end of the return pipe 20 is connected to one end of the catalyst riser 16. One end of the reaction product pipe 22 is connected to the cracking and reforming reactor 12, and another end of the reaction product pipe 22 is connected to the distillation unit which is not shown. The fuel pipe 24 is connected to the heating tank 14. An air pipe is branched to an air pipe 26a and an air pipe 26b, and the air pipe 26a is connected to the heat tank 14 and the air pipe 26b is connected to the withdrawing pipe 18. The exhaust pipe 28 is connected to the heating tank 14.

The cracking and reforming reactor 12 is used for bringing the oil feedstock into contact with the fluidized bed-state aromatic production catalyst A to obtain a reaction product containing a large amount of BTX. The cracking and reforming reactor 12 includes a first supply port, a withdrawing port, a cyclone 13, a discharge port, and a second supply port. The first supply port of the cracking and reforming reactor 12 is a port through which a vapor of the oil feedstock and the aromatic production catalyst A that have been transferred through the catalyst riser 16 are introduced into the inside of the cracking and reforming reactor 12. The withdrawing port of the cracking and reforming reactor 12 is a port through which the aromatic production catalyst A is withdrawn to the withdrawing pipe 18. The cyclone 13 separates the reaction product vapor and the aromatic production catalyst A. The discharge port of the cracking and reforming reactor 12 is a port through which the reaction product vapor separated by the cyclone 13 is discharged into the reaction product pipe 22. The second supply port of the cracking and reforming reactor 12 is a port through which the oil feedstock that has been supplied through the feed pipe 4a is introduced into the inside of the cracking and reforming reactor 12.

The heating tank 14 is used to actively heat the aromatic production catalyst A, using not only the heat generated by combustion of the coke adhered to the aromatic production catalyst A, but also energy supplied from an external source. In other words, the heating tank 14 itself is a large heating unit. The heat tank 14 is provided with a first supply port, a withdrawing port, a second supply port, a third supply port, a cyclone 15, and an exhaust port. The first supply port of the heat tank 14 is a port through which the aromatic production catalyst A that has been transported through the withdrawing pipe 18 is introduced into the inside of the heat tank 14. The withdrawing port of the heating tank 14 is a port through which the aromatic production catalyst A is withdrawn from the heating tank 14 into the return pipe 20. The second supply port of the heating tank 14 is a port through which the tower bottom oil (heating fuel), and the like, supplied from, for example, the distillation unit which is not shown, via the fuel pipe 24 is introduced into the inside of the heating tank 14.

The third supply port of the heat tank 14 is a port through which air (oxygen-containing gas) supplied from an air blower via the air pipe 26a is introduced into the inside of the heating tank 14. The cyclone 15 separates combustion gas generated by the combustion and the aromatic production catalyst A. The exhaust port of the heating tank 14 is a port through which combustion gas separated by the cyclone 15 is exhausted from the heating tank 14 into the exhaust pipe 28.

The heating tank can be provided in a plurality of stages; for example in two stages. In other words, it is possible to take measures such as suppressing degradation of the aromatic production catalyst A by providing two heating tanks and increasing the heating temperature within the individual heating tanks in a stepwise manner.

The catalyst riser 16 is provided with a first supply port, and a second supply port. The catalyst riser 16 extends upward in a vertical direction and has a pipe shape, and the first supply port thereof is a port through which the aromatic production catalyst A that has been transferred through the return pipe 20 is introduced into the inside of the catalyst riser 16. The second supply port of the catalyst riser 16 is a port through which the oil feedstock that has been supplied through a feed pipe 4b is introduced into the inside of the catalyst riser 16.

The heating device 2 heats the oil feedstock in advance before introducing the oil feedstock into the above cracking and reforming reaction apparatus 10 and forms a two-phase gas-liquid stream. The heating device 2 is configured by a furnace, a heat exchanger, or a combination of a plurality of them or the like. The heating device 2 of the present embodiment has a not shown heat exchanger exchanging heat with a produced oil (tower bottom oil and the like) that has been passed through the reaction product pipe 22 and has been supplied from the not shown distillation unit provided at the downstream side of the reaction product pipe 22, and heating the oil feedstock. The heating device 2 is provided with a supply port and a discharge port. The supply port of the heating device 2 is a port through which the oil feedstock is introduced into the inside the heating device 2. The discharge port of the heating device 2 is a port through which the oil feedstock that has become to the two-phase gas-liquid stream by heating is fed to a feedstock feeding pipe 6. In addition, one end of the feedstock feeding pipe 6 is connected to the heating device 2, and another end thereof is connected to the gas-liquid separator 3.

The gas-liquid separator 3 separates the oil feedstock that has become to the two-phase gas-liquid stream into a gas fraction 7a and a liquid fraction 7b. The gas-liquid separator 3 of the present embodiment is provided with a tank having a certain capacity, and uses a tank system in which the two-phase gas-liquid stream in the inside of the tank formed from the oil feedstock is separated into the gas fraction 7a and the liquid fraction 7b. In addition, as the gas-liquid separator 3, a cyclone system and the like in which the two-phase gas-liquid stream is formed to be a swirl flow and separated in a centrifugal way can be adopted. The gas-liquid separator 3 is provided with a supply port, a discharge port, and a withdrawing port. The supply port of the gas-liquid separator 3 is a port through which the oil feedstock that has supplied through the feedstock feeding pipe 6 and is in a gas-liquid two-phase state is introduced inside of the gas-liquid separator 3. The discharge port of the gas-liquid separator 3 is a port through which the gas fraction 7a is discharged to the feed pipe 4a. The withdrawing port of the gas-liquid separator 3 is a port through which the liquid fraction 7b is withdrawn to the feed pipe 4b.

The feed pipe 4a, 4b are the pipes in which the gas fraction 7a and the liquid fraction 7b that have been separated from the oil feedstock, are separately introduced at different positions of the cracking and reforming reaction apparatus 10 described above. In addition, in order to introduce the oil feedstock into the cracking and reforming reaction apparatus 10 through the feed pipes 4a, 4b, it is preferable to use a transferring device and the like which uses a carrier gas such as steam. One end of the feed pipe 4a is connected to the gas-liquid separator 3 and another end is connected to the cracking and reforming reactor 12 of the cracking and reforming reaction apparatus 10. In addition, the connecting position of the one end of the feed pipe 4a is required to be upward of a gas-liquid interface in the tank of the gas-liquid separator 3, and the connection position thereof is arranged at the top of the tank in the present embodiment. One end of the feed pipe 4b is connected to the gas-liquid separator 3 and another end is connected to the catalyst riser 16 of the cracking and reforming reaction apparatus 10. In addition, the connecting position of the one end of the feed pipe 4b is required to be downward of the gas-liquid interface in the tank of the gas-liquid separator 3, and the connecting position thereof is arranged at the bottom of the tank in the present embodiment.

<Producing Method of Monocyclic Aromatic Hydrocarbons>

Production of aromatic hydrocarbons using the production plant 1 illustrated in FIG. 1 is performed, for example, in a method described below.

(Heating Step)

First, before introducing the oil feedstock into the cracking and reforming reaction apparatus 10, the oil feedstock is heated by the heat device 2. In the heat device 2, the supplied oil feedstock is heated by exchanging heat with the produced oil supplied from the distillation unit by the not shown heat exchanger, and furthermore, is heated by not shown furnace, and part thereof is vaporized and forms a two-phase gas-liquid stream. Then, the oil feedstock that has become to the two-phase gas-liquid stream is transferred to the gas-liquid separator 3 through the feedstock feed pipe 6. In the gas and liquid ratio of the two-phase gas-liquid stream, the gas ratio is more than or equal to 1% by weight and preferably more than or equal to 5% by weight. If the gas ratio is less than 1% by weight, a heat recovery amount reduces, and a disadvantage in which a reaction heat lacks in the reactor occurs. The upper limit is desirable to be high, however, is limited by the temperature level of the heat source based on design.

The oil feedstock used in the present invention is an oil having a 10 volume % distillation temperature of more than or equal to 140° C. and a 90 volume % distillation temperature of less than or equal to 380° C. With an oil having a 10 volume % distillation temperature of less than 140° C., the reaction involves production of monocyclic aromatic hydrocarbons from light compounds, and thus, it departs from the spirit of producing monocyclic aromatics from the oil feedstock containing polycyclic aromatic hydrocarbons in the plant according to the present invention. Further, if an oil having a 90 volume % distillation temperature of more than 380° C. is used, then the yield of monocyclic aromatic hydrocarbons tends to decrease, and the amount of coke deposition on the monocyclic aromatic hydrocarbon production catalyst tends to increase, causing a more rapid deterioration in the catalytic activity.

The 10 volume % distillation temperature of the oil feedstock is preferably more than or equal to 150° C., and the 90 volume % distillation temperature of the oil feedstock is preferably less than or equal to 360° C.

In this description, the 10 volume % distillation temperature and the 90 volume % distillation temperature refer to values measured in accordance with the methods prescribed in JIS K 2254 "Petroleum products—determination of distillation characteristics".

Examples of oil feedstocks having a 10 volume % distillation temperature of more than or equal to 140° C. and a 90 volume % distillation temperature of less than or equal to 380° C. include cracked light oils (LCO) produced in a fluid catalytic cracking unit, hydrotreated refined oil of LCO, coal liquefaction oil, hydrocracked oil from heavy oils, straight-run kerosene, straight-run gas oil, coker kerosene, coker gas oil, and hydrocracked oil from oil sands.

Polycyclic aromatic hydrocarbons included in these oil feedstocks exhibit low reactivity and are difficult to convert to monocyclic aromatic hydrocarbons in the cracking and reforming reaction step of the present invention. On the other hand, these polycyclic aromatic hydrocarbons are hydrogenated in the hydrogenation reaction step and converted to naphthenobenzenes, and if these naphthenobenzenes are then recycled and re-supplied to the cracking and reforming reaction step, they can be converted to monocyclic aromatic hydrocarbons. However, among polycyclic aromatic hydrocarbons, tricyclic or higher-cyclic aromatic hydrocarbons consume a large amount of hydrogen in the hydrogenation reaction step, and suffer from poor reactivity in the cracking and reforming reaction step even in the form of a hydrogenation reaction product, and therefore the oil feedstock preferably does not contain a large amount of such tricyclic or higher-cyclic aromatic hydrocarbons. Accordingly, the amount of tricyclic or higher-cyclic aromatic hydrocarbons within the oil feedstock is preferably less than or equal to 25 volume %, and more preferably less than or equal to 15 volume %.

Examples of particularly desirable oil feedstocks which contain bicyclic aromatic hydrocarbons that can be converted to naphthenobenzenes in the hydrogenation reaction step, but in which the amount of tricyclic or higher-cyclic aromatic hydrocarbons is reduced, include oil feedstocks having a 90 volume % distillation temperature of more than or equal to 330° C.

In this description, the polycyclic aromatic hydrocarbons describe the combined total of the amount of bicyclic aromatic hydrocarbons (the bicyclic aromatics) and the amount of tricyclic or higher-cyclic aromatic hydrocarbons (the tricyclic or higher-cyclic aromatics), which is either measured in accordance with JPI-5S-49 "Petroleum Products—Determination of Hydrocarbon Types—High Performance Liquid Chromatography", or determined by analysis using FID gas chromatography or two-dimensional gas chromatography. In the following description, the amount of polycyclic aromatic hydrocarbons, bicyclic aromatic hydrocarbons or tricyclic or higher-cyclic aromatic hydrocarbons reported using the units "volume %" represents the amount that has been measured in accordance with JPI-5S-49, whereas the amount that is reported using the units "% by mass" represents the amount that has been measured on the basis of FID gas chromatography or two-dimensional gas chromatography.

When using such oil feedstock, the heating temperature of the oil feedstock by the heating device 2 is set to, for example, 150 to 350° C. and thereby at least one component contained in the oil feedstock is vaporized and the two-phase gas-liquid stream can be formed. In addition, by pre-heating, part of the heat required for the aromatic production reaction in the cracking and reforming reactor 12 can be provided to the oil feedstock.

(Gas-Liquid Separation Step)

Next, the oil feedstock that has become to the two-phase gas-liquid stream is separated into the gas fraction 7a and the liquid fraction 7b by the gas-liquid separator 3. In the gas-liquid separator 3, the oil feedstock that has been transferred from the heating device 2 through the feedstock feeding pipe 6 is introduced into the inside of the tank and is separated into the gas fraction 7a and the liquid fraction 7b. The gas fraction 7a and the liquid fraction 7b are separated from the oil feedstock in such a manner that the gas fraction 7a is accumulated at the top of the inside of the tank of the gas-liquid separator 3, and the liquid fraction 7b is accumulated at the bottom of the inside of the tank of the gas-liquid separator 3. The gas fraction 7a of oil feedstock is discharged to the feed pipe 4a connected at the top of the inside of the tank of the gas-liquid separator 3, and the liquid fraction 7b of the feedstock is withdrawn to the feed pipe 4b connected to the bottom of the inside of the tank of the gas-liquid separator 3.

(Introducing Step)

Next, the gas fraction 7a and the liquid fraction 7b that have been separated into gas and liquid from the oil feedstock are separately introduced at different positions of the cracking and reforming reaction apparatus 10 by the feed pipes 4a, 4b. In the present embodiment, the gas fraction 7a discharged from the top of the tank by the feed pipe 4a is introduced into the cracking and reforming reactor 12 in the cracking and reforming reaction apparatus 10. In addition, the liquid fraction 7b withdrawn from the bottom of the tank by the feed pipe 4b is introduced into the catalyst riser 16 of the cracking and reforming reaction apparatus 10.

According to this, in the feed pipe 4b, only the liquid fraction 7b of the oil feedstock flows therein. Thus, when the oil feedstock is introduced into the catalyst riser 16, the flow resistance is maintained in approximately constant in the vicinity of the introducing part. That is, it is possible to prevent vibration of the feed pipe 4b as shown in the conventional art introducing the two-phase gas-liquid stream in which the vibration thereof is caused as a result of the repeatedly change of the flow resistance in the vicinity of the introducing part by introducing sequentially a liquid and a gas having different viscosities and the like, into the catalyst riser. This operation and effects are obtained also in the feed pipe 4a in which the gas fraction 7a of the oil feedstock only flows therein. Therefore, it is possible to prevent the generation of vibration when the oil feedstock is introduced into the cracking and reforming reaction apparatus 10.

In addition, the liquid fraction 7b of the oil feedstock is preferably introduced into the catalyst riser 16 as the present embodiment. The reason is because by introducing the liquid fraction 7b of the oil feedstock into the catalyst riser 16, the liquid fraction 7b of the oil feedstock is heated by the aromatic production catalyst A flowing inside of the catalyst riser 16 and heated by the heating tank 14, and while introducing it into the cracking and reforming reactor 12, the whole or at least part thereof can be vaporized. In addition, the gas fraction 7a of the oil feedstock is preferably introduced into the cracking and reforming reactor 12 as the present embodiment. The reason is because the gas fraction 7a of the oil feedstock is already vaporized. In addition, the gas fraction 7a of the oil feedstock can be introduced to the catalyst riser 16. In this case, in the catalyst riser 16, the introducing position of the gas fraction 7a of the oil feedstock is preferably arranged at the downstream side (close to the cracking and reforming reactor 12) of the introducing position of the liquid fraction 7b of the oil feedstock.

In addition, as shown in FIG. 1, the introduction of the gas fraction 7a of the oil feedstock, the liquid fraction 7b of the oil feedstock and steam is controlled by overhead pressure control of the tank of the gas-liquid separator 3, flow control of steam and temperature control of the oil feedstock, but it depends on the ratio between the liquid fraction and gas fraction. For example, it is desirable to control the introduction of the gas fraction 7a, the liquid fraction 7b and steam while making the following adjustments.

(1) Controlling the ratio of the liquid fraction and the introducing amount of steam.
(2) Controlling the overhead pressure of the tank of the gas-liquid separator 3.
(3) Controlling by cascade control the liquid surface of the gas-liquid separator 3 at a flow rate of cold feed (the feedstock before being introduced into the heating device 2).
(4) Controlling by cascade control the temperature of the oil feedstock at the discharge port of the heating device 2 by adjusting the introducing amount of the fuel for heating the heating device 2.

(Aromatic Hydrocarbon Production Step)

As above described, the gas fraction 7a of the oil feedstock is introduced continuously into the cracking and reforming reactor 12 from the feed pipe 4a, and the liquid fraction 7b of the oil feedstock is introduced continuously into the catalyst riser 16 from the feed pipe 4b. At the same time, the aromatic production catalyst A that has been heated in the heating tank 14 is introduced continuously into the catalyst riser 16 from the return pipe 20, and is transported into the cracking and reforming reactor 12 by the vapor of the oil feedstock, which rises up the inside of the catalyst riser 16 and acts as a transport medium.

The aromatic production catalyst A that is introduced continuously together with the vapor of the oil feedstock into the cracking and reforming reactor 12 from the catalyst riser 16 is converted to a fluidized-bed state by the vapor of the oil feedstock. The oil feedstock vapor and the aromatic production catalyst A are brought into contact with each other within this fluidized-bed state, yielding a reaction product vapor that contains a large amount of BTX. The reaction product vapor and the aromatic production catalyst A are separated by the cyclone 13, and the reaction product vapor is discharged continuously into the reaction product pipe 22. Coke adheres to the catalyst as a result of the contact with the oil feedstock vapor, and part of the partially inactivated aromatic production catalyst A is withdrawn continuously from the cracking and reforming reactor 12 into the withdrawing pipe 18.

By combusting the heating fuel, which is supplied from an external source through the fuel pipe 24, in the presence of the air (oxygen-containing gas) that is supplied from the air blower through the air pipe 26a, the aromatic production catalyst A that has been introduced continuously into the heating tank 14 from the withdrawing pipe 18 is heated continuously to a temperature more than or equal to the reaction temperature inside the cracking and reforming reactor 12. Further, during this heating, the coke adhered to the aromatic production catalyst A also combusts, and thus, the aromatic production catalyst A undergoes regeneration during the heating process. The combustion gases generated by the combustion are discharged continuously into the exhaust pipe 28. The heated aromatic production catalyst A is withdrawn continuously from the heating tank 14 into the return pipe 20, and is then re-introduced into the catalyst riser 16 from the return pipe 20. In this manner, the aromatic production catalyst A is continuously circulated between the cracking and reforming reactor 12 and the heating tank 14.

The amount of coke that adheres to the aromatic production catalyst A upon bringing the oil feedstock and the aromatic production catalyst A into contact with each other is not necessarily sufficient to produce the amount of heat necessary to the cracking and reforming reactor 12 being supplied by combusting the coke. Accordingly, in order to enable efficient and stable production of a reaction product containing monocyclic aromatic hydrocarbons from the above types of oil feedstocks, a cracking and reforming reaction apparatus 10 that includes a heating tank 14 is particularly effective.

(Aromatic Production Catalyst)

The aromatic production catalyst A is a catalyst for producing the monocyclic aromatic hydrocarbons and contains a crystalline aluminosilicate.

[Crystalline Aluminosilicate]

The crystalline aluminosilicate is preferably a medium pore size zeolite and/or a large pore size zeolite, as these materials enable the yield of the monocyclic aromatic hydrocarbons to be further increased.

Medium pore size zeolites are zeolites having a 10-membered ring basic structure, and examples of these medium pore size zeolites include zeolites having AEL, EUO, FER, HEU, MEL, MFI, NES, TON and WEI type crystal structures. Among these, MFI-type zeolites are preferable because they enable a greater increase in the yield of monocyclic aromatic hydrocarbons.

Large pore size zeolites are zeolites having a 12-membered ring basic structure, and examples of these large pore size zeolites include zeolites having AFI, ATO, BEA, CON, FAU, GME, LTL, MOR, MTW and OFF type crystal structures. Among these, BEA, FAU and MOR type zeolites are preferable in terms of industrial usability, and BEA-type zeolites are desirable as they enable a greater increase in the yield of monocyclic aromatic hydrocarbons.

Besides the above medium pore size zeolites and large pore size zeolites, the crystalline aluminosilicate may also contain small pore size zeolites having a 10-membered ring or smaller basic structure, and extra-large pore size zeolites having a 14-membered ring or larger basic structure.

Examples of the small pore size zeolites include zeolites having ANA, CHA, ERI, GIS, KFI, LTA, NAT, PAU and YUG type crystal structures.

Examples of the extra-large pore size zeolites include zeolites having CLO and VPI type crystal structures.

In those cases where the cracking and reforming reaction step is conducted as a fluidized-bed reaction, the amount of the crystalline aluminosilicate within the monocyclic aromatic hydrocarbon production catalyst, relative to a value of 100% by mass for the entire catalyst, is preferably within a range from 20 to 60% by mass, more preferably from 30 to 60% by mass, and still more preferably from 35 to 60% by mass. Provided the amount of the crystalline aluminosilicate is at least 20% by mass, the yield of monocyclic aromatic hydrocarbons can be increased satisfactorily. However, if the amount of the crystalline aluminosilicate exceeds 60% by mass, then the amount of binder that can be included in the catalyst decreases, and the resulting catalyst may be unsuitable for a fluidized-bed.

In addition, in those cases where the cracking and reforming reaction step is conducted as a fixed bed reaction, the amount of the crystalline aluminosilicate within the monocyclic aromatic hydrocarbon production catalyst, relative to a value of 100% by mass for the entire catalyst, is preferably within a range from 60 to 100% by mass, more preferably from 70 to 100% by mass, and still more preferably from 90 to 100% by mass. Provided the amount of the crystalline aluminosilicate is at least 60% by mass, the yield of monocyclic aromatic hydrocarbons can be increased satisfactorily.

[Phosphorus, Boron]

The monocyclic aromatic hydrocarbon production catalyst preferably also includes phosphorus and/or boron. If the monocyclic aromatic hydrocarbon production catalyst includes phosphorus and/or boron, then a deterioration over time in the yield of monocyclic aromatic hydrocarbons can be prevented, and coke production on the catalyst surface can be inhibited.

The methods for incorporating phosphorus within the monocyclic aromatic hydrocarbon production catalyst include methods in which phosphorus is supported on a crystalline aluminosilicate, crystalline aluminogallosilicate or crystalline aluminozincosilicate, methods in which a phosphorus compound is added during synthesis of the zeolite, thereby substituting a portion of the internal framework of the crystalline aluminosilicate with phosphorus, and methods in which a crystallization promoter containing phosphorus is used during synthesis of the zeolite, by ion-exchange methods and impregnation methods, for example. Although there are no particular limitations on the phosphate ion-containing aqueous solution used in the above methods, a solution prepared by dissolving phosphoric acid, diammonium hydrogen phosphate, ammonium dihydrogen phosphate or another water-soluble phosphate salt or the like in water at an arbitrary concentration can be used favorably.

The methods for incorporating boron within the monocyclic aromatic hydrocarbon production catalyst include methods in which boron is supported on a crystalline aluminosilicate, crystalline aluminogallosilicate or crystalline aluminozincosilicate, methods in which a boron compound is added during synthesis of the zeolite, thereby substituting a portion of the internal framework of the crystalline aluminosilicate with boron, and methods in which a crystallization promoter containing boron is used during synthesis of the zeolite, by ion-exchange methods and impregnation methods, for example.

The amount of phosphorus and boron included in the monocyclic aromatic hydrocarbon production catalyst, relative to the total mass of the catalyst, is preferably within a range from 0.1 to 10% by mass, wherein the lower limit is more preferably not less than 0.5% by mass, and the upper limit is more preferably not more than 9% by mass, and still more preferably not more than 8% by mass. Provided the amount of phosphorus relative to the total mass of the catalyst is at least 0.1% by mass, any deterioration over time in the yield of the monocyclic aromatic hydrocarbons can be prevented, and provided the amount of phosphorus is not more than 10% by mass, the yield of the monocyclic aromatic hydrocarbons can be increased.

[Gallium, Zinc]

If necessary, gallium and/or zinc may be included in the monocyclic aromatic hydrocarbon production catalyst. Including gallium and/or zinc can improve the rate of production of monocyclic aromatic hydrocarbons.

Examples of the form of the gallium contained within the monocyclic aromatic hydrocarbon production catalyst include catalysts in which the gallium is incorporated within the lattice framework of the crystalline aluminosilicate (crystalline aluminogallosilicates), catalysts in which gallium is supported on the crystalline aluminosilicate (gallium-supporting crystalline aluminosilicates), and catalysts including both of these forms.

Examples of the form of the zinc contained within the monocyclic aromatic hydrocarbon production catalyst include catalysts in which the zinc is incorporated within the lattice framework of the crystalline aluminosilicate (crystalline aluminozincosilicates), catalysts in which zinc is supported on the crystalline aluminosilicate (zinc-supporting crystalline aluminosilicates), and catalysts including both of these forms.

A crystalline aluminogallosilicate or a crystalline aluminozincosilicate has a structure in which $SiO_4$, $AlO_4$, and $GaO_4$ structures exist within the framework. In addition, a crystalline aluminogallosilicate or crystalline aluminozincosilicate can be obtained, for example, by gel crystallization via hydrothermal synthesis, by a method in which gallium or zinc respectively is inserted into the lattice framework of a crystalline aluminosilicate, or a method in which aluminum is inserted into the lattice framework of a crystalline gallosilicate or crystalline zincosilicate respectively.

A gallium-supporting crystalline aluminosilicate can be obtained by supporting gallium on a crystalline aluminosilicate using a conventional method such as an ion-exchange method or impregnation method. There are no particular limitations on the gallium source used in these methods, and examples include gallium salts such as gallium nitrate and gallium chloride, and gallium oxide.

A zinc-supporting crystalline aluminosilicate can be obtained by supporting zinc on a crystalline aluminosilicate using a conventional method such as an ion-exchange method or impregnation method. There are no particular limitations on the zinc source used in these methods, and examples include zinc salts such as zinc nitrate and zinc chloride, and zinc oxide.

In those cases where the monocyclic aromatic hydrocarbon production catalyst contains gallium and/or zinc, the amount of gallium and zinc within the monocyclic aromatic hydrocarbon production catalyst, relative to a value of 100% for the total mass of the catalyst, is preferably within a range from 0.01 to 5.0% by mass, and more preferably from 0.05 to 2.0% by mass. Provided the amount of gallium and/or zinc is more than or equal to 0.01% by mass, the rate of production of monocyclic aromatic hydrocarbons can be increased, and provided the amount is less than or equal to 5.0% by mass, the yield of monocyclic aromatic hydrocarbons can be improved.

[Form]

The monocyclic aromatic hydrocarbon production catalyst is used in the form of a powder, granules or pellets or the like, depending on the reaction format. For example, a catalyst in form of powder is used in the case of a fluidized bed represented as the present embodiment, whereas a catalyst in form of granules or pellets is used in the case of a fixed bed represented as other embodiments. The average particle size of the catalyst used in a fluidized bed is preferably within a range from 30 to 180 μm, and more preferably from 50 to 100 μm. Further, the powder density of the catalyst used in a fluidized bed is preferably within a range from 0.4 to 1.8 g/cc, and more preferably from 0.5 to 1.0 g/cc.

The average particle size describes the particle size at which the particle size distribution obtained by classification using sieves reaches 50% by mass, whereas the powder density refers to the value measured using the method prescribed in JIS R 9301-2-3.

In order to obtain a catalyst in granular or pellet form, if necessary, an inert oxide may be added to the catalyst as a binder, with the resulting mixture then molded using any of various molding apparatus.

In those cases where the monocyclic aromatic hydrocarbon production catalyst contains an inorganic oxide such as a binder, a compound that contains phosphorus may be used as the binder.

The heating fuel acts as an additional fuel besides the coke adhered to the aromatic production catalyst A, and examples of this heating fuel include fuels supplied from externally (so-called torch oil), such as the tower bottom oil from the distillation unit. In terms of avoiding the problem of degradation of the aromatic production catalyst A caused by steam, the heating fuel is preferably a tower bottom oil having a comparatively large ratio of carbon atoms to hydrogen atoms (C/H).

Examples of the oxygen-containing gas include air and pure oxygen, although air is preferable from an economic viewpoint.

Because the heat required by the aromatic production reaction inside the cracking and reforming reactor 12 is supplied by the aromatic production catalyst A heated by the heat tank 14, the heating of the oil feedstock by the heating device 2 may be performed to any temperature less than the reaction temperature inside the cracking and reforming reactor 12, and is preferably within a range from 150 to 350° C.

(Reaction Temperature)

Although there are no particular limitations on the reaction temperature during contact of the oil feedstock with the monocyclic aromatic hydrocarbon production catalyst and subsequent reaction, a reaction temperature of 400 to 650° C. is preferable. Provided the lower limit of the reaction temperature is at least 400° C., the oil feedstock can be reacted with relative ease. The lower limit is more preferably 450° C. or higher. On the other hand, provided the upper limit temperature is not more than 650° C., the yield of monocyclic aromatic hydrocarbons can be increased. The upper limit is more preferably 600° C. or lower.

(Reaction Pressure)

The reaction pressure during contact of the oil feedstock and a recycle oil described hereafter with the monocyclic aromatic hydrocarbon production catalyst and subsequent reaction is preferably less than or equal to 1.5 MPaG, and more preferably less than or equal to 1.0 MPaG. Provided the reaction pressure is not more than 1.5 MPaG, the generation of by-product light gases can be prevented, and the pressure resistance required for the reaction apparatus can be lowered.

(Contact Time)

There are no particular limitations on the contact time between the oil feedstock and the monocyclic aromatic hydrocarbon production catalyst, provided the desired reaction proceeds satisfactorily, but in terms of the gas transit time across the monocyclic aromatic hydrocarbon production catalyst, a time of 1 to 300 seconds is preferable. The lower limit of this time is more preferably more than or equal to 5 seconds, and the upper limit is more preferably less than or equal to 150 seconds. Provided the contact time is more than or equal to 1 second, a reliable reaction can be achieved, whereas provided the contact time is less than or equal to 300 seconds, deposition of carbon matter on the catalyst due to an excess coking or the like can be suppressed, and the amount of light gas generated by cracking can also be suppressed.

The amount of the aromatic production catalyst A withdrawn from the cracking and reforming reactor 12 (namely, the circulation amount) is preferably within a range from 5 to 30 tons per 1 ton of the oil feedstock supplied to the cracking and reforming reactor 12. This amount is also determined in accordance with the overall heat balance.

The pressure inside the heating tank 14 is preferably higher than the pressure inside the cracking and reforming reactor 12 in order to facilitate transport of the heated aromatic production catalyst A heated by the heating tank 14 to the cracking and reforming reactor 12.

In the case of a two-stage heating process, if the first heating tank is located in a lower position than the second heating tank, then the pressure inside the first heating tank must be set to a higher pressure than that inside the second heating tank to enable transport of the aromatic production catalyst A heated by the heating tank 14 into the second heating tank. The pressure inside the first heating tank 14 is preferably approximately 0.1 MPa higher than the pressure inside the second heating tank, and is preferably more than or equal to 0.2 MPa, and more preferably more than or equal to 0.9 MPa.

The lower limit of the pressure inside the second heating tank is preferably 0.1 MPaG, more preferably 0.2 MPaG, and still more preferably 0.3 MPaG. The upper limit is preferably 0.8 MPaG, more preferably 0.7 MPaG, and still more preferably 0.6 MPaG.

Because the heat required by the aromatic production reaction inside the cracking and reforming reactor 12 is supplied by the aromatic production catalyst A heated by the heating tank 14, the temperature inside the heating tank 14 must be at least as high as the reaction temperature inside the cracking and reforming reactor 12, and is preferably within a range from 500 to 800° C., and more preferably from 600 to 700° C.

In the case of a two-stage heating process, because the heat required by the aromatic production reaction inside the cracking and reforming reactor 12 must be supplied by the aromatic production catalyst A heated by the heating tanks, the temperature of the first heating tank is preferably more than or equal to the reaction temperature inside the cracking and reforming reactor 12. Further, in order to suppress hydrothermal degradation of the aromatic production catalyst A by the high-temperature steam generated upon combustion of the heating fuel, the temperature inside the first heating tank is preferably lower than the temperature inside the second heating tank. Specifically, the temperature inside the first heating tank is preferably less than or equal to 650° C., and more preferably less than or equal to 630° C.

Because the heat required by the aromatic production reaction inside the cracking and reforming reactor 12 is supplied by the aromatic production catalyst A heated by the heating tanks, the lower limit of the temperature inside the second heating tank is preferably the reaction temperature inside the cracking and reforming reactor 12, and is more preferably 500° C., and still more preferably 600° C. In contrast, the upper limit of the temperature is preferably 800° C., and more preferably 700° C.

The amount of the heating fuel supplied to the heating tank 14 (in the case of a tower bottom oil) is preferably within a range from 0.005 to 0.08 tons, per 1 ton of the oil feedstock supplied to the cracking and reforming reactor 12, with this amount being determined in accordance with the amount of coke deposited and the overall heat balance.

In the case of a two-stage heating process, as a general principle, the total amount of the heating fuel is preferably supplied to the first heating tank.

In the producing method of monocyclic aromatic hydrocarbons in the present invention described as above, the method includes the steps of introducing the oil feedstock having a 10 volume % distillation temperature of more than or equal to 140° C. and a 90 volume % distillation temperature of less than or equal to 380° C. into the cracking and reforming reaction apparatus 10, bringing the oil feedstock and the aromatic production catalyst A into contact with each other, and producing reaction products including monocyclic aromatic hydrocarbons, and the method includes the steps of heating the oil feedstock in advance before the introducing step and forming the two-phase gas-liquid stream, separating the two-phase gas-liquid stream into the gas fraction and the liquid fraction, and introducing separately the gas fraction and the liquid fraction at different positions of the cracking and reforming reaction apparatus 10. Accordingly, the two-phase gas-liquid stream of the oil feedstock is not introduced into the cracking and reforming reaction apparatus 10 from one position, and the gas fraction and the liquid fraction is separately introduced at different positions of the cracking and reforming reaction apparatus 10. Thus, it is possible to prevent that the flow resistance changes repeatedly in the vicinity of the introducing part and thereby vibration of the pipes.

Therefore, according to the present embodiment, it is possible to prevent the generation of vibration when the oil feedstock is introduced.

While exemplary embodiments of the invention have been described above with reference to the drawings, the above embodiments are not to be considered as limitative of the present invention. Each means, and shapes, combinations and the like of the constituent members illustrated in the above embodiments are merely examples, and various modifications based on design requirements and the like can be made without departing from the scope of the present invention.

For example, in the introduction of the liquid fraction of the oil feedstock into the catalyst riser, it may be vaporized by heating by using the steam.

DESCRIPTION OF REFERENCE SIGNS

1: monocyclic aromatic hydrocarbon production plant
2: heating device
3: gas-liquid separator
4a, 4b: feed pipe (introducing device)
7a: vapor fraction
7b: liquid fraction
10: cracking and reforming reaction apparatus
12: cracking and reforming reactor
14: heating tank
16: catalyst riser (catalyst transfer pipe)
A: aromatic production catalyst

The invention claimed is:

1. A producing method of monocyclic aromatic hydrocarbons in which reaction products including monocyclic aromatic hydrocarbons are produced by bringing an oil feedstock and an aromatic production catalyst into contact with each other, the oil feedstock having a 10 volume % distillation temperature of more than or equal to 140° C. and a 90 volume % distillation temperature of less than or equal to 380° C., the method comprising the steps of:
   introducing the oil feedstock into a cracking and reforming reaction apparatus housing the aromatic production catalyst;
   bringing the oil feedstock and the aromatic production catalyst into contact with each other in the cracking and reforming reaction apparatus housing the aromatic production catalyst;
   heating the oil feedstock in advance before introducing the oil feedstock into the cracking and reforming reaction apparatus and forming a two-phase gas-liquid stream;
   separating the two-phase gas-liquid stream into a gas fraction and a liquid fraction; and
   introducing the gas fraction and the liquid fraction at different positions of the cracking and reforming reaction apparatus to convert the fractions of the oil feedstock to monocyclic aromatic hydrocarbons.

2. The producing method of monocyclic aromatic hydrocarbons according to claim 1, wherein
   the cracking and reforming reaction apparatus is provided with
   a cracking and reforming reactor housing the aromatic production catalyst,
   a heat tank heating the aromatic production catalyst withdrawn from the inside of the cracking and reforming reactor by a combustion, and
   a catalyst transfer pipe transferring the aromatic production catalyst heated at the heat tank to the cracking and reforming reactor,
   wherein in the step of introducing, at least the liquid fraction is introduced into the catalyst transfer pipe.

3. The producing method of monocyclic aromatic hydrocarbons according to claim 2, wherein
   in the step of introducing, at least the gas fraction is introduced into the cracking and reforming reactor.

\* \* \* \* \*